United States Patent
Filippova et al.

(10) Patent No.: US 9,023,399 B2
(45) Date of Patent: *May 5, 2015

(54) WATER-SOLUBLE ANTI-INFLAMMATORY CREAM WITH NATURAL INGREDIENTS BASE

(71) Applicant: NU Technology, LLC, Union Dale, PA (US)

(72) Inventors: Irina V Filippova, Union Dale, PA (US); Leonid K. Filippov, Union Dale, PA (US)

(73) Assignee: NU Technology, LLC, Union Dale, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/906,399

(22) Filed: May 31, 2013

(65) Prior Publication Data
US 2014/0141088 A1 May 22, 2014

Related U.S. Application Data

(63) Continuation-in-part of application No. 13/678,613, filed on Nov. 16, 2012.

(51) Int. Cl.
| | |
|---|---|
| *A61K 9/06* | (2006.01) |
| *A61K 36/886* | (2006.01) |
| *A61K 33/04* | (2006.01) |
| *A61K 33/30* | (2006.01) |
| *A61K 31/375* | (2006.01) |
| *A61K 31/7028* | (2006.01) |
| *A61K 38/39* | (2006.01) |
| *A61K 31/355* | (2006.01) |
| *A61K 31/045* | (2006.01) |
| *A61K 31/125* | (2006.01) |
| *A61K 31/60* | (2006.01) |
| *A61K 31/192* | (2006.01) |
| *A61K 31/07* | (2006.01) |
| *A61K 45/06* | (2006.01) |
| *A61K 9/00* | (2006.01) |
| *A61K 8/64* | (2006.01) |
| *A61Q 19/00* | (2006.01) |
| *A61K 8/92* | (2006.01) |
| *A61K 8/97* | (2006.01) |
| *A61K 8/11* | (2006.01) |
| *A61K 31/05* | (2006.01) |
| *A61K 31/095* | (2006.01) |
| *A61K 31/315* | (2006.01) |
| *A61L 26/00* | (2006.01) |

(52) U.S. Cl.
CPC . *A61K 9/06* (2013.01); *A61K 31/07* (2013.01); *A61K 31/125* (2013.01); *A61K 31/192* (2013.01); *A61K 31/355* (2013.01); *A61K 31/375* (2013.01); *A61K 31/60* (2013.01); *A61K 31/7028* (2013.01); *A61K 33/04* (2013.01); *A61K 33/30* (2013.01); *A61K 36/886* (2013.01); *A61K 38/39* (2013.01); *A61K 45/06* (2013.01); *A61K 9/0014* (2013.01); *A61K 8/64* (2013.01); *A61Q 19/00* (2013.01); *A61K 8/922* (2013.01); *A61K 8/97* (2013.01); *A61K 8/11* (2013.01); *A61K 31/05* (2013.01); *A61K 31/095* (2013.01); *A61K 31/315* (2013.01); *A61L 26/0057* (2013.01); *A61L 26/0066* (2013.01); *A61L 2300/30* (2013.01); *A61L 2300/41* (2013.01); *A61L 2300/62* (2013.01)

(58) Field of Classification Search
USPC ......... 424/490, 642, 705, 725, 726, 730, 732, 424/736, 744, 745, 764, 765, 766, 769, 776
See application file for complete search history.

(56) References Cited

U.S. PATENT DOCUMENTS

| | | | |
|---|---|---|---|
| 4,364,940 A | 12/1982 | Neiss et al. | |
| 4,543,351 A | 9/1985 | Messina | |
| 4,767,750 A | 8/1988 | Jacquet et al. | |
| 5,080,901 A * | 1/1992 | Hangay et al. | 424/764 |
| 5,344,850 A | 9/1994 | Hata et al. | |
| 5,393,461 A | 2/1995 | Fillipova | |
| 5,470,884 A | 11/1995 | Corless et al. | |
| 5,476,852 A | 12/1995 | Cauwenbergh | |
| 5,654,013 A | 8/1997 | Taylor et al. | |
| 5,667,790 A | 9/1997 | Sellers, Jr. | |
| 5,688,522 A | 11/1997 | Hardy | |
| 5,690,947 A * | 11/1997 | Habif et al. | 424/401 |

(Continued)

FOREIGN PATENT DOCUMENTS

| | | | | |
|---|---|---|---|---|
| FR | 2334367 A * | 8/1977 | | A61K 8/97 |
| FR | 2813194 A1 * | 3/2002 | | A61K 8/27 |
| RU | 2220736 C1 * | 1/2004 | | |
| WO | WO98/17329 | 4/1998 | | |
| WO | WO 2005097084 | 10/2005 | | |
| WO | WO 2006096955 | 9/2006 | | |

OTHER PUBLICATIONS

Rose hip: retrieved from internet: http://en.wikipedia.org/wiki/Rose_hip. Retrieved on Feb. 5, 2014.*
Saeedi, M. et al. "The Treatment of Atopic Dermatitis with Licorice Gel", J. Dermatolog Treat. Sep. 2003. Abstract.
Stewart, J.C.M. et al. "Treatment of Severe and Moderately Severe Atopic Dermatitis with Evening Primrose Oil (Epogam): a Multi-centre Study", www.researchgate.net, Jul. 2009. Abstract.
Office Action mailed Jul. 26, 2013 for U.S. Appl. No. 13/737,114, filed Jan. 9, 2013.
Notice of Allowance with Examiner's Amendment and Reasons for Allowance mailed Nov. 12, 2013 for U.S. Appl. No. 13/737,114, filed Jan. 9, 2013.

*Primary Examiner* — Ernst V Arnold
*Assistant Examiner* — Hong Yu
(74) *Attorney, Agent, or Firm* — Joseph E. Maenner; Maenner & Associates, LLC

(57) ABSTRACT

A water-soluble anti-inflammatory cream is disclosed. The cream is a composition of between about 7.5% and about 30% by weight of a healing oil; between about 1% and about 6% by weight of an herbal extract; between about 0% and about 3.5% by weight of microencapsulated amino acids; and at least 39.4% by weight water.

15 Claims, No Drawings

(56) References Cited

U.S. PATENT DOCUMENTS

| | | |
|---|---|---|
| 5,696,099 A | 12/1997 | della Valle et al. |
| 5,698,593 A | 12/1997 | Peck |
| 5,837,270 A | 11/1998 | Burgess |
| 5,952,372 A | 9/1999 | McDaniel |
| 5,972,993 A | 10/1999 | Ptchelintsev |
| 5,976,565 A | 11/1999 | Fotinos |
| 5,994,330 A | 11/1999 | El Khoury |
| 6,333,093 B1 | 12/2001 | Burrell et al. |
| 6,987,133 B2 | 1/2006 | Chen |
| 7,262,179 B2 | 8/2007 | Court et al. |
| 7,364,732 B2 | 4/2008 | Thompson et al. |
| 7,732,574 B2 | 6/2010 | Kelly et al. |
| 8,192,749 B2 | 6/2012 | Ashley |
| 8,268,367 B2 | 9/2012 | Choudhary et al. |
| 8,268,790 B2 | 9/2012 | McDonagh et al. |
| 8,313,782 B2 | 11/2012 | Guthery |
| 8,613,961 B1 * | 12/2013 | Filippova et al. ............. 424/725 |
| 2003/0198687 A1 | 10/2003 | Bennett et al. |
| 2004/0059110 A1 * | 3/2004 | Nakano et al. .................. 544/60 |
| 2004/0234628 A1 | 11/2004 | Kearns et al. |
| 2004/0254245 A1 * | 12/2004 | Lintner ........................ 514/560 |
| 2005/0032900 A1 | 2/2005 | Krauser |
| 2005/0058728 A1 * | 3/2005 | Randolph et al. ............ 424/732 |
| 2005/0255076 A1 | 11/2005 | Santo et al. |
| 2006/0057092 A1 * | 3/2006 | Marion ...................... 424/70.13 |
| 2007/0027217 A1 | 2/2007 | Ehrlich |
| 2007/0154402 A1 | 7/2007 | Trumbore et al. |
| 2007/0154575 A1 * | 7/2007 | Shimoda et al. .............. 424/756 |
| 2008/0233060 A1 * | 9/2008 | Grune ............................. 424/59 |
| 2008/0286384 A1 | 11/2008 | Reichert |
| 2008/0317795 A1 | 12/2008 | Traynor et al. |
| 2009/0068128 A1 * | 3/2009 | Waddington .................... 424/59 |
| 2010/0215634 A1 | 8/2010 | Tennenbaum et al. |
| 2011/0159077 A1 | 6/2011 | Figueroa Lizama |
| 2011/0177014 A1 * | 7/2011 | Guay et al. ..................... 424/62 |
| 2011/0207696 A1 | 8/2011 | Mailland et al. |
| 2012/0225107 A1 | 9/2012 | Hechavarria |
| 2013/0101662 A1 | 4/2013 | Carreno Ralma et al. |

* cited by examiner

WATER-SOLUBLE ANTI-INFLAMMATORY CREAM WITH NATURAL INGREDIENTS BASE

CROSS-REFERENCE TO RELATED APPLICATION

The present application is a Continuation-in-Part application of U.S. patent application Ser. No. 13/678,613, filed on Nov. 16, 2012, which is incorporated by reference herein in its entirety.

FIELD OF THE INVENTION

The present invention relates to a water-soluble anti-inflammatory cream with natural ingredients base to treat burn, wound, injury, and scar site in a patient.

The present invention relates to topical compositions of: (a) mixture of plant oils having biologically active ingredients, (b) water-soluble ibuprofen (and/or other NSAIDs), (c) water-soluble microencapsulated sulfur, and zinc oxide, (d) active natural herbal extracts, (e) amino acids, and (f) water-soluble microencapsulated vitamins C and A.

BACKGROUND OF THE INVENTION

Burns and other skin wounds are not only traumatic in and of themselves, but the opening of the skin due to the burn/wound invites infection and other secondary medical issues. In its early stage, the inflammation process in a pure burn/wound is preceded by bleedings, extravasations, and blood coagulation factors including leukocyte migration into the burn/wound from surrounding tissues and blood vessels. In a later phase (after about 24 hours), poorly developed monocytes (containing larger amounts of extracellular burn/wound material) are located in the perivascular connective tissue adjacent to the burn/wound. It is crucially important in the healing process at the burn/wound.

Prior art water-soluble creams used in the cleaning process of a burn/wound coincide with an increase in growth factors and cytokines stimulating migration proliferation, and differentiation of burn/wound cells providing the healing. If the burn/wound is the inflammation phase, the following two goals must be achieved: burn/wound cleaning and debridement, and disinfection. The first goal is typically achieved with hypertonic solutions, water-soluble creams, and proteolytic enzymes. The second goal is typically achieved with chemotherapy and antiseptics.

BRIEF SUMMARY OF THE INVENTION

Briefly, the present invention provides a water-soluble anti-inflammatory cream that is a composition of between about 7.5% and about 30% by weight of a healing oil; between about 1% and about 6% by weight of an herbal extract; between about 0% and about 3.5% by weight of microencapsulated amino acids; and at least 39.4% by weight water.

DETAILED DESCRIPTION OF THE INVENTION

Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The inventive cream is a therapeutic, nontoxic, water-soluble and bio-degradable composition that provides the following advantages: (1) a protective barrier that prevents the burn/wound from progressing through healthy tissue; (2) the cream is a sterile, water-soluble composition that is non-toxic and a skin non-irritant; (3) the cream moisturizes the burn/wound area, soothing the skin and thereby minimizing trauma or tissue damage; and (4) the cream is believed by the inventors to be safe for use on all types of burns/wounds.

If the superficial layers of the epidermis are characterized by local erytherma (redness) and light edema (swelling), then the burn is of the first degree. Second degree burns involve a damage extended to the dermis, more marked ederma and formation of blisters containing serous exudates. Third degree burns are a true destruction of the structural elements of the skin and a formation of blisters, sores, charred zones and shock, and acute intoxication.

An exemplary purpose of a water-soluble anti-inflammatory cream for treatment of a burn/wound is the prevention of burn/wound desiccation. Inflammation of the burn/wound area, including neutrophil and macrophage migration, is one of the principal problems in the healing process.

The primary contact of a water-soluble anti-inflammatory cream with blood surrounding the burn/wound may induce a rapid complement and coagulation factors binding, resulting in complementary leukocyte activation, chemotaxis, and cytokine production. In a moist environment of a water-soluble anti-inflammatory cream neutrophils and macrophages, burn/wound cells process a high rate of cleaning and destroying, degrading, and removal of non-vital tissue. The water-soluble anti-inflammatory cream according to the present invention, containing an extracellular matrix protein, can promote migration and proliferation of cells, contributing to burn/wound healing.

Exemplary creams according to the present invention are described below. The inventors have formulated several compositions of cream using a natural ingredients base in the form of a water-soluble complex emulsion/suspension using the technology as disclosed in U.S. Pat. No. 5,393,461 entitled "PREPARATION OF STABLE AQUEOUS EMULSION OF WATER-INSOLUBLE PARTICLES", which is incorporated herein by reference in its entirety. The inventive cream is in the form of a stable water-soluble emulsion/suspension in a temperature range between about 59° F. (about 15° C.) and about 95° F. (about 35° C.).

The microencapsulation process disclosed in U.S. Pat. No. 5,393,461 is a process that enhances through-the-skin penetration of biological active ingredients through the normal, dry, and mature skin. The complex emulsion/suspension (herein after referred to simply as an "emulsion") disclosed in U.S. Pat. No. 5,393,461 is an emulsion in which a dispersed phase contains another dispersed phase. The multiple emulsion is a water/oil/water (W/O/W) emulsion. A W/O/W emulsion is a system in which water globules are dispersed in oil globules, the latter being themselves dispersed in an aqueous phase. Multiple emulsions are sometimes called triple-phase emulsions. Multiple emulsion includes two immiscible liquids (water or oil); therefore, their preparation demands the presence of two emulsifiers (the primary and the secondary surfactants). A solid part of the product (or cream) consists of fine particles (with size of less than about 1 micron) of sulfur and zinc oxide.

An active ingredient of the cream is microencapsulated water-soluble USP ibuprofen. Ibuprofen, in a class of drugs called nonsteroidal anti-inflammatory drug (NSAID), belonging to the group of propionic acid derivatives, inhibits the enzyme cyclo-oxygenase (prostaglandin synthesis), which catalyzes the transformation of unsaturated fatty acids to prostaglandins. It is believed that the inhibition of the prostaglandin synthesis is the cause for the analgesic, antipyreti, and anti-inflammatory action of the drug. Ibuprofen works by reducing hormones that cause inflammation and pain in the body. Ibuprofen is used to reduce the fever, pain, inflammation, and stiffness caused by many conditions.

The inventors recognize that long-term or extensive ingestion of NSAID can result in the drugs having toxicity to the kidneys and also to the lining of the stomach, possibly causing ulcers. Therefore, inventors are using the technology disclosed in U.S. Pat. No. 5,393,461 to produce microencapsulated USP ibuprofen in the form of a stable water-soluble emulsion for burn/wound/injury/scar treatment.

Exemplary compositions of a cream for burn/wound/injury/scar treatment contain water-soluble microencapsulated ibuprofen and natural biological active ingredient, including sulfur, zinc oxide, vitamin C and vitamin A. The inventors have found that the inventive creams reduce inflammation and pain, stimulate antibacterial and antimicrobial activities, decrease transdermal water loss, reduce irritation, itching, and discomfort of the skin, and stimulate of blood circulation.

The inventive creams using water-soluble microencapsulated ibuprofen and/or other NSAIDs (between about 0% and about 15% by weight) include at least some of the following:

(i) Arylpropionic acids (e.g., ibuprofen, flurbiprofen, fenoprofen, naproxen, and oxaprozin), (ii) Salicylic acid derivatives (e.g., aspirin, salsalate, sodium salicylate, choline magnesium trisalicylate, sulfasalazine, olsalazine, and diflunisal), (iii) Anthranilic acids (e.g., mefenamic acid and meclofenamic acid), (iv) Heteroaryl acids (e.g., tolmetin, diclofenac, and ketorolac), (v) Enolic acids (e.g., piroxicam and meloxicam), (vi) Indole and Indene acetic acids (e.g., indomethacin and sulindac), (vii) Indole acteic acids (e.g., etodolac), (viii) Para-Aminophenol derivatives (e.g., acetaminophen or Tylenol®)

(ix) Alkanes (e.g., Nabumetone), (x) Diaryl-Substituted furanones (e.g., rofecoxib), (xi) Diaryl-Substituted pyrazoles (e.g., celecoxib), and (xii) Sulfonanilides (e.g., nimesulide).

The inventive cream also includes at least some of the natural ingredients listed below.

Microencapsulated Water-Soluble USP Sulfur

Sulfur is a vital ingredient for dermatological products. Sulfur is an excellent natural preservative since it has anti-inflammatory, anti-bacterial and anti-fungal properties. Exemplary medical uses of sulfur preparations are as fungicides and parasiticides, and for the treatment of various cutaneous disorders such as psoriasis, seborrhoea, eczema-dermatitis, and lupus erythermatosus. Sulfur kills bacteria on and in the skin. Sulfur converts to pentatonic acids in order to exert germicidal activity. Sulfur also possesses a keratolytic property, which is the basic property needed to treat certain cutaneous disorders unassociated with infection. The inventive creams include between about 0% and about 8% by weight of microencapsulated USP sulfur.

Microencapsulated Water-Soluble USP Zinc Oxide

Zinc oxide has been used in the treatment of literally hundreds of skin disorders and it has been at least partially successful in many of them. Zinc oxide has a mild astringent and antiseptic action. Zinc oxide is a Category I skin protector, and promotes healthy skin. Zinc oxide is used for treatment of skin diseases and infections such as eczema, impetigo, ringworm, varicose ulcers, pruritus, and psoriasis.

Zinc oxide regulates the activity of oil glands and is required for protein, DNA and RNA synthesis and collagen formation. Zinc oxide provides an excellent barrier to the sun and other irritants.

The inventors have produced microencapsulated USP zinc oxide in the form of the stable water-soluble emulsion/suspension for dermatological application. The common active ingredient used in derma cream compositions is zinc oxide. Zinc oxide in the form of fine particles (with a size of less than about 1 micron) is an astringent and antiseptic action principal remaining use is in the skin disorder treatment. The inventive creams include between about 0% and about 15% by weight of microencapsulated USP zinc oxide.

Microencapsulated USP Vitamin C

Vitamin C (ascorbic acid) is reversibly oxidizable in the human body to a form known as dehydroascorbic acid. The physiological functions of vitamin C are related to this oxidation-reduction system. Vitamin C is involved in carbohydrate metabolism, reduction of glucose tolerance, and decrease of hepatic glycogen content and resistance to insulin. Vitamin C prevents the oxidation of epinephrine. A very important role of vitamin C is to decrease the rate of skin aging process and to increase the wound-healing process. Unique properties of vitamin C are that it: (i) stimulates: (1) blood circulation, (2) cell regeneration, (3) skin immune system, (4) fibroblasts and keratinocytes to produce collagen, and (5) dermal penetration of the active ingredients through the skin, (ii) is an anti-inflammatory agent, (iii) increases skin metabolism, (iv) activates dermal enzymes, and (v) promotes faster healing due to quicker absorption and prolonged duration. Vitamin C is an antioxidant that is required for at least 300 metabolic functions in the body, including tissue growth and repair, adrenal gland function, and healthy gums.

However, vitamin C is unstable and quickly oxidizes with time. In order to decrease the rate of oxidation and increase the biological activity of vitamin C, the inventors have produced microencapsulated USP Vitamin C in the form of a stable water-soluble emulsion for dermatological application. The inventive creams include between about 0% and about 4.5% by weight of microencapsulated vitamin C.

Microencapsulated Water-Soluble Vitamin A

Vitamin A (Retinol A) has a number of important functions in the body. Vitamin A is essential for the integrity of epithelial cells and has a stabilizing effect on various membranes. Vitamin A also regulates membrane permeability and stimulates the synthesis of nuclear RNA, suggesting a role in genetic transcription and cell differentiation. Vitamin A is converted to a metabolite that is a true vitamin. Vitamin A is used for local treatments of infections, burns, and wounds.

Vitamin A is an anti-oxidant, which is a compound that may protect against disease by neutralizing unstable oxygen molecules, called free radicals, within the body. Vitamin A is involved in night vision, growth, cell differentiation and reproduction. Vitamin A also maintains the health of the skin (prevents acne and dermatitis) and surface tissues especially those with mucous linings. These linings are the body first defense against infection, which is why vitamin A helps fight colds and infections.

However, vitamin A is also unstable and quickly oxidizes with time. In order to decrease the rate of its oxidations and increase the biological activity of vitamin A, and the inventors have developed microencapsulated USP Vitamin A in the form of the stable water-soluble emulsion for dermatological application. The inventive creams include between about 0% and about 0.5% by weight of vitamin A.

Natural Healing Oils

Natural healing oils included in the inventive creams may include blackcurrants seed oil, borage seed oil, dog rose hip oil, hazel nut oil, tamanu oil, sesame oil, chamomile oil, grape seed oil, lavender oil, clove oil, kiwi seed oil, tea tree oil, safflower oil, thymus oil. The inventive creams include between about 7.5% and about 30% by weight of healing oils.

Herbal Extracts

Additionally, biological active herbal extracts included in the creams may include birch leave and bark extract, black nightshade extract, burdock extract, goldenseal extract, bilberry extract, *calendula officinalis* flower extract, carrot seed extract, comfrey leaf extract, grapefruit seed extract, olive leaves extract, St. John's wort extract, willow bark extract. The inventive creams include between about 0% and about 6% by weight of herbal extracts.

Amino Acids

The inventive creams may also include essential and non-essential amino acids. The inventive creams may include between about 0% and about 6% by weight of microencapsulated amino acids.

Other Ingredients

The inventive creams also include combinations of at least two of Decyl-glycoside (between about 0% and about 8% by weight), microencapsulated collagen peptides (between about 2% and about 6% by weight), microencapsulated menthol (between about 0% and about 1.5% by weight), microencapsulated camphor (between about 0% and about 2% by weight), microencapsulated salicylic acid (between about 0.3% and about 0.5% by weight), Aloe Barbadensis leaf extract (between about 0% and about 2% by weight), microencapsulated vitamin E (about 0.1% by weight), non-ionic surfactants and wetting agents (between about 0.01% and about 5% by weight), and water (between about 39.4% and about 79.4% by weight).

Exemplary compositions of the inventive creams are provided below. While the exemplary compositions listed below give percentages of ingredients by weight, it is contemplated that the weight percent of each ingredient may vary as much as ±5% of the total weight of the composition.

Natural Burn Cream Composition

| Ingredients | Weight Percent (%) |
| --- | --- |
| microencapsulated Sulfur | 8 |
| microencapsulated Vitamin C | 2.5 |
| microencapsulated Vitamin A | 0.5 |
| microencapsulated collagen peptides | 2.0 |
| microencapsulated Menthol | 3.5 |
| microencapsulated Camphor | 3.0 |
| Healing Oil | 21 |
| Herbal Extract | 4.0 |
| microencapsulated Amino Acids | 3.0 |
| microencapsulated Salicylic Acid | 0.5 |
| microencapsulated vitamin E (da Tocopherol) | 0.1 |
| Water | Remainder to 100% |

The inventors have found that the inventive burn cream generates a moist, anti-inflammation, anti-bacterial, and anti-microbial environment around a burn surface, thereby promoting fast recovery (in particular, suppurative burn) without infections. The inventive burn cream also decreases the risk of formation of colloid and hypertrophied scars and skin implantation.

Natural Wound Cream with Vitamin C Composition

| Ingredients | Weight Percent (%) |
| --- | --- |
| microencapsulated Sulfur | 6 |
| microencapsulated Vitamin C | 3.0 |
| microencapsulated Vitamin A | 0.5 |
| microencapsulated collagen peptides | 2.0 |
| microencapsulated Menthol | 3.5 |
| microencapsulated Camphor | 3.0 |
| Healing Oil | 22 |
| Herbal Extract | 6.0 |
| microencapsulated Amino Acids | 3.0 |
| microencapsulated Salicylic Acid | 0.5 |
| microencapsulated Vitamin E (da Tocopherol) | 0.1 |
| Water | Remainder to 100% |

The inventors have found that the inventive wound cream with microencapsulated vitamin C provides a moist, anti-inflammation, anti-bacterial, and anti-microbial environment around a wound surface, promoting a fast recovery (in particular suppurative wound) and reducing or even preventing skin infections. The combination of natural healing oils, natural wound cream with vitamin C, and ibuprofen cream dissolves solid pus and solid necrosis, promoting fast healing of deep wounds, in particular, diabetic and necrosis cases.

Natural Anti-Scar Cream Composition

| Ingredients | Weight Percent (%) |
| --- | --- |
| microencapsulated Sulfur | 7 |
| microencapsulated Vitamin C | 4.5 |
| microencapsulated Vitamin A | 0.5 |
| microencapsulated collagen peptides | 6.0 |
| microencapsulated Camphor | 1.0 |
| Healing Oil | 20 |
| Herbal Extract | 4.0 |
| microencapsulated Amino Acids | 3.5 |
| microencapsulated Vitamin E (da Tocopherol) | 0.2 |
| Water | Remainder to 100% |

The inventors have found that the inventive anti-scar cream provides soothing and softening effect on the skin, restoring skin to healthy state. The inventive cream diminishes and improves the overall appearance and texture of scars. The inventive cream may also help remove a scar without surgery.

Natural Wound Cream Composition

| Ingredients | Weight Percent (%) |
| --- | --- |
| microencapsulated Sulfur | 6 |
| microencapsulated Zinc Oxide | 3.5 |
| microencapsulated Vitamin A | 0.5 |
| microencapsulated collagen peptides | 2.0 |
| microencapsulated Menthol | 1.5 |
| microencapsulated Camphor | 2.0 |
| Healing Oil | 26 |
| microencapsulated Amino Acids | 3.0 |
| Herbal Extract | 6.0 |
| microencapsulated Salicylic Acid | 0.5 |
| microencapsulated Vitamin E (da Tocopherol) | 0.2 |
| Water | Remainder to 100% |

The inventors have found that the inventive wound cream provides a moist, anti-inflammatory, anti-bacterial, and anti-microbial environment around wounds, cuts, and scraped skin surfaces to quickly heal (in particular suppurative burn and wound) and reduce or even prevent skin infections. Inventive wound cream provides nourishing and calming effects on damaged skin.

Ibuprofen Cream Composition

| Ingredients | Weight Percent (%) |
| --- | --- |
| microencapsulated Ibuprofen | 15 |
| Healing Oil | 25 |
| Herbal Extract | 1.0 |
| microencapsulated Vitamin E (da Tocopherol) | 0.1 |
| Water | Remainder to 100% |

The inventors have found that the water-soluble ibuprofen cream provides a moist and anti-inflammatory environment around damaged skin surface, in particular suppurative damaged skin, and also reduces or prevents skin infections. The inventors have further found that a combination of natural healing oils, natural wound cream with vitamin C, and ibuprofen cream dissolves solid pus and solid necrosis, and promotes quick recovery of deep wounds and burns, in particular, for diabetic and necrosis cases.

Natural Zinc Oxide Cream for Regenerating Skin Composition

| Ingredients | Weight Percent (%) |
| --- | --- |
| Microencapsulated Sulfur | 5 |
| microencapsulated Zinc Oxide | 15.0 |
| microencapsulated collagen peptides | 5.0 |
| Healing Oil | 30 |
| Herbal Extract | 2.0 |
| microencapsulated Vitamin E (da Tocopherol) | 0.1 |
| Water | Remainder to 100% |

The inventors have found that the inventive zinc oxide cream for regenerating skin regenerates damaged skin (i.e., wounds, 1st to 3rd degree burns, cuts).

Natural Wound/Burn/Injury/Scar Cleaner & Moisturizer

| Ingredients | Weight Percent (%) |
| --- | --- |
| Decyl-Glycoside | 8 |
| Healing Oil | 7.5 |
| Herbal Extract | 2.5 |
| microencapsulated Salicylic Acid | 0.3 |
| *Aloe Barbadensis* leaf extract | 2.0 |
| microencapsulated Vitamin E (da Tocopherol) | 0.1 |
| Water | Remainder to 100% |

The inventors have found that the inventive wound/burn/injury/scar cleaner and moisturizer occludes a burn/wound/injury/scar, controls infection level, and promotes healing by maintaining the burn/wound areas at a certain moisture level. The moist dressing system also uniformly distributes moisture, the inventive cleaner and moisturizer cream, and fluids through the burn/wound/injury/scar areas, and prevents or reduces the size and number of dry spots covering the burn/wound.

According to the present invention, the scar cleaner and moisturizer may provide the benefits of providing an optimum environment for burn/wound healing; providing pain relief; providing healing properties; does not have or induce unpleasant odor; provides impermeability to exogenous bacteria, prevention of proliferation of burn/wound/injury/scar surface flora and reduction of burn/wound/injury/scar bacterial concentration; and does not produce a negative effect on burn/wound/injury/scar regeneration.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A water-soluble cream comprising:
   between about 7.5% and about 30% by weight of a healing oil, wherein the healing oil comprises blackcurrents seed oil, borage seed oil, oil, dog rose hip oil, hazel nut oil, tamanu oil, sesame oil, chamomile oil, and grape seed oil;
   between about 1% and about 6% by weight of an herbal extract;
   between about 0% and about 3.5% by weight of microencapsulated amino acids; and
   at least 39.4% by weight water.

2. The water-soluble cream according to claim 1, further comprising a microencapsulated ingredient comprising between about 0% and about 8% by weight of sulfur.

3. The water-soluble cream according to claim 1, further comprising a microencapsulated ingredient comprising between about 0% and about 15% by weight of zinc oxide.

4. The water-soluble cream according to claim 1, further comprising a microencapsulated ingredient comprising between about 0% and about 4.5% by weight of vitamin C (Ascorbic acid).

5. The water-soluble cream according to claim 1, further comprising a microencapsulated ingredient comprising between about 0% and about 3% by weight of collagen peptides.

6. The water-soluble cream according to claim 1, further comprising a microencapsulated ingredient comprising between about 0% and about 0.5% by weight of vitamin E (dN-Tocopherol).

7. The water-soluble cream according to claim 1, further comprising a microencapsulated ingredient comprising between about 0% and about 0.2% by weight of vitamin A.

8. The water-soluble cream according to claim 1, further comprising a microencapsulated ingredient comprising between about 0% and about 4% by weight of menthol.

9. The water-soluble cream according to claim 1, further comprising a microencapsulated ingredient comprising between about 0% and about 3.5% by weight of camphor.

10. The water-soluble cream according to claim 1, further comprising a microencapsulated ingredient comprising between about 0% and about 0.5% by weight of salicylic acid.

11. The water-soluble cream according to claim 1, further comprising between about 0% and about 8% by weight of decyl-glycoside.

12. The water-soluble cream according to claim 1, further comprising between about 0% and about 2% by weight of Aloe Barbadensis leaf extract.

13. The water-soluble cream according to claim 1, further comprising a microencapsulated ingredient comprising between about 0% and about 15% by weight of ibuprofen.

14. The water-soluble cream according to claim 1, wherein the herbal extract consists of birch leave and bark extract, *calendula officinalis* flower extract, grapefruit seed extract, olive leaves extract, and willow bark extract.

15. A water-soluble cream comprising:
   between about 7.5% and about 30% by weight of a healing oil comprising blackcurrants seed oil, borage seed oil, dog rose hip oil, hazel nut oil, tamanu oil, sesame oil, chamomile oil, and grape seed oil;

between about 1% and about 6% by weight of an herbal extract, wherein the herbal extract comprises birch leave and bark extract, *calendula officinalis* flower extract, grapefruit seed extract, olives leaves extract, and willow bark extract;

between about 0% and about 3.5% by weight of microencapsulated amino acids; and at least 39.4% by weight water.

\* \* \* \* \*